United States Patent [19]

Persson

[11] Patent Number: 4,566,334
[45] Date of Patent: Jan. 28, 1986

[54] ULTRASONIC DETECTOR DEVICE

[76] Inventor: Hans A. W. Persson, Iliongränd 90, S-223 71 Lund, Sweden

[21] Appl. No.: 618,481

[22] Filed: Jun. 8, 1984

[30] Foreign Application Priority Data

Jun. 14, 1983 [SE] Sweden .................................. 8303366

[51] Int. Cl.⁴ ............................................ G01N 29/00
[52] U.S. Cl. ........................................ 73/649; 310/336
[58] Field of Search ................. 73/649, 658, 661, 587; 310/322, 334, 336, 337, 338

[56] References Cited

U.S. PATENT DOCUMENTS 2,875,354  2/1959  Harris ............................. 310/322 X
4,461,179  7/1984  Holt .................................... 73/658

Primary Examiner—Jerry W. Myracle
Attorney, Agent, or Firm—Barnes, Kisselle, Raisch, Choate, Whittemore & Holbert

[57] ABSTRACT

This invention relates to a novel design of a microprobe for measuring intensity distribution, instantaneous intensity values and acoustic signal shapes of ultrasound. The probe consists of a rod-shaped electrode which is fixed with the aid of an electrically and acoustically insulating material in a sleeve-shaped electrical shield. To one end surface of said device is adhered a piezoelectric film such that the film will come in contact with the end surfaces of the electrode, the insulating material and the electrical shield. As only the outer surface of the piezoelectric film is covered by an electrically conductive layer, the rod-shaped electrode on the inner side of the film will determine the active surface of the probe.

10 Claims, 5 Drawing Figures

ULTRASONIC DETECTOR DEVICE

BACKGROUND OF THE INVENTION

This invention relates to an ultrasonic detector for converting ultrasonic signals into electrical signals, particularly for measuring instantaneous intensity values at well-defined points.

With the increasing application of the ultrasonic techniques in medical diagnostic and therapy there also follows an essentially increased need for characterization of the ultrasonic transducer. It is necessary for instance to control that the acoustic energy emitted does not exceed a limit value which may be dangerous to the patient or the operator. The most customary method of performing these measurements makes use of very sensitive balances in liquid baths. These balances measure the ultrasonic pressure which is proportional to the acoustic energy emitted (Carson et al. 1978, Ultrasound in Med. & Biol., Vol. 3, pp. 341–350). For performing this type of measurement use can also be made of the heat produced at the absorption of the acoustic energy (Torr et al. 1977, Phys. Med. Biol. 22, pp. 444–450).

In the two aforementioned methods, the mean value of the acoustic energy emitted is measured. However, to obtain the relative intensity distribution or instantaneous intensity values other methods are required, one of them being the acousto-optical method. This method makes use of refraction effects or interference of optical signals with the acoustic signal (Reibold 1977, Acustica Vol. 36, pp. 214–220). Being complicated, this method is applied in special cases only.

A more interesting method is to measure with the aid of a detector device being in the form of a microprobe. The active material in such a probe is a piezoelectric material in the size of 1 mm or less, which converts the acoustic signal into an electrical signal. With such a measuring probe it is possible by simple means to measure the extension and instantaneous values of the acoustic energy from the transducer and, in certain cases, also the appearance of the acoustic signal (Lewin 1981, Ultrasonics sep. pp. 213–216).

Hitherto, the microprobes have suffered from the disadvantage of being difficult to produce because the measuring probe shall have a small active surface and internal oscillations and reflections in the probe can hardly be avoided. Such oscillations and reflections must be prevented in order that the acoustic signal shape may be registered. Besides a very good electrical shielding of the probe is necessary to prevent a disturbance of the measuring result by capacitive coupling of the excitation signal to the measuring probe. Normally, there is used for such probes a piezoelectric material which is coated with electrodes of for example nickel or aluminum on both sides, of U.S. Pat. No. 4,316,115. The above-mentioned drawback of such probes give rise to difficult insulation and connection problems because of the double-sided coating.

SUMMARY OF THE INVENTION

In a novel design of a detector device in the form of a microprobe the above-mentioned drawbacks have been eliminated by the use of a piezoelectric film having a coating on only one side thereof. Despite its simple design the probe has a high sensitivity and satisfactory electrical shielding simultaneously as internal oscillations and reflections are minimized. A further advantage of this design is that the active surface can be made very small without any complication of the production.

DESCRIPTION OF THE PREFERRED EMBODIMENT

Figure 1:
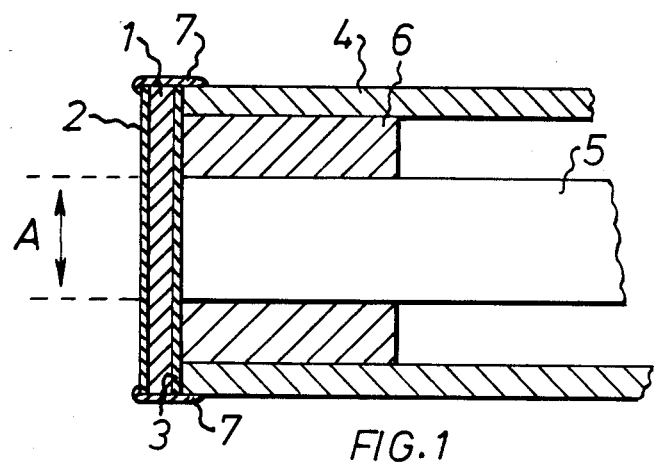
FIG. 1 shows an enlarged part of the basic design of the mocroprobe.

FIG. 1 illustrates an example of a possible design of the microprobe. The active material 1 is in the form of a disk consisting of a piezoelectric film, such as the plastic film PVDF (polyvinyl difluoride). Normally, this plastic film is coated with electrically conductive layers on both sides between which an electric signal is registered when the plastic film is exposed to an acoustic signal.

In this case, however, the plastic film is coated with an electrically conductive layer 2 on the front face only. The other face of the plastic film is adhered by means of a thin glue layer 3 to the distal end of a device comprising a metal sleeve 4, a metal rod 5 and a hard, but simultaneously porous and electrically insulating sleeve 6. The metal sleeve 4 constitutes an electrically conductive casing enclosing the metal rod 5 so as to form a shield therefor. The porous sleeve 6 centers the metal rod 5 in the metal sleeve 4 and also serves as a support for the plastic film between the metal sleeve 4 and the metal rod 5. The active surface A corresponds to that part of the piezoelectric plastic film 1 which is covered by the end surface of the metal rod 5. Said metal rod will, in fact, function as an electrode on the rear face of the film. The metal layer 2 on the front face is electrically connected to the metal sleeve 4 with the aid of conductive lacquer 7. Finally, the other, proximal, end of the metal sleeve 4 and the metal rod 5, respectively, is connected to a coaxial cable 8 according to FIG. 2. The part of an acoustic signal that impinges on the active surface A can thus be registered as an electrical signal at the terminal end of the coaxial cable.

It should be observed that the piezoelectric film need not necessarily cover the end surface of the metal sleeve 4. It is sufficient for the film to cover the electrode 5 and parts of the insulating sleeve 6, i.e. to extend beyond the entire end surface of the electrode, so that one does not risk to have electrical contact established between the electrode 5 and electrically conductive layer 2.

Many advantages are associated with this novel design. The metal layer 2, the conductive lacquer 7 and the metal sleeve 4 provide an excellent electrical shielding. The active surface A is determined as to its size only by the end surface of the metal rod 5 and therefore can be made small without any complication of the production of the probe. The value of the acoustic impedance (density x sound velocity) of the plastic film lies close to the value of the acoustic impedance of the investigation medium (water). This gives an effective transmission of the acoustic signal into the plastic film 1, thus providing good possibilities of high sensitivity. After transmission through the plastic film the major part of the acoustic signal is reflected back from the boundary surface between the plastic film 1 and the metal rod 5. This is due to the metal rod having a nearly 10 times higher acoustic impedance value compared with the plastic film. The incoming and reflected signals will interfere and thus affect the sensitivity of the detector device. In the case described, there occurs a reflection towards a higher impedance (the metal rod), which does not produce any phase shift of the reflected signal compared with the incoming signal. Further, there is chosen for the plastic film a minimal thickness ($<1/10\lambda$) in relation to the wavelength $\lambda$ of the acoustic signal in the plastic film. This means that the part of the incoming signal and the part of the reflected signal which are simultaneously present in the plastic film will work together and increase sensitivity. Compared with the case where no reflection is obtained between the plastic film and the underlying material, sensitivity increases nearly by a factor 2. It should be mentioned that the metal layer 2 and the glue layer 3 are very thin compared with the plastic film and do not influence the acoustic signal.

The part of the acoustic energy which nevertheless passes into the metal rod 5 can give undesirable internal interfering echoes. However, these echoes have been eliminated in that the proximal end of the metal rod 5 has been given the shape of a cone. Alternatively, the sound energy in the rod can be damped in other prior art ways, for instance by providing a damping mass or by manufacturing the rod from an electrically conductive, but absorbing material.

It should also be emphasized that the detector device is entirely insensitive to acoustic signals which impinge on the metal sleeve 4 or the plastic film 1 around the active area A. This is due to the material inside these parts (air, porous sleeve) has a very low acoustic impedance and high absorption. The acoustic signal will therefore be reflected for the most part while the remainder will be absorbed and not reach the metal rod and thus not either the active surface A of the plastic film.

Figure 2:
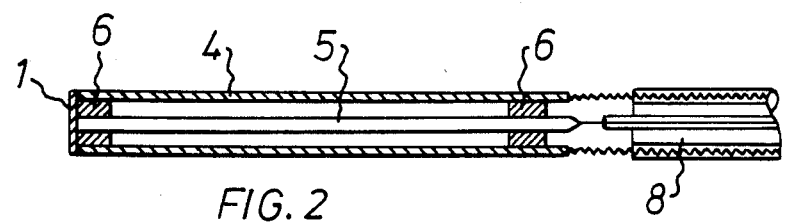
FIG. 2 shows the entire basic design of the probe.
Figure 3:
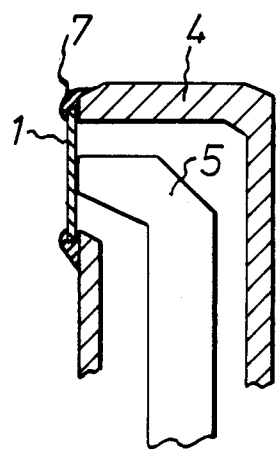
FIG. 3 shows an alternative embodiment of the probe.
Figure 4:
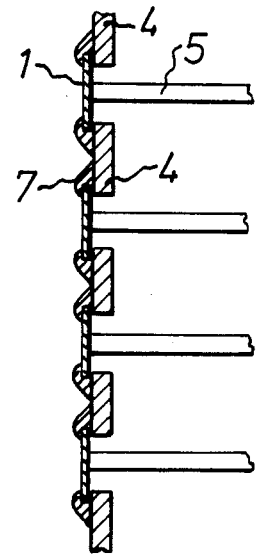
FIG. 4 shows an alternative embodiment of the probe equipped with several electrodes.
Figure 5:
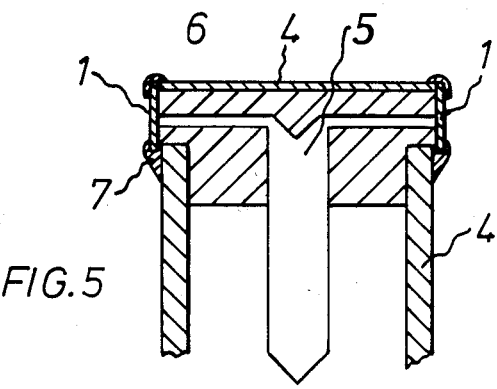
FIG. 5 shows an alternative embodiment with a 360° sensitivity range.

It should be pointed out that the embodiments of the invention illustrated in FIGS. 1 and 2 should only be considered as examples of a conceivable embodiment of a detector device. Alternatively, for instance the piezoelectric film may wholly or partly cover one or more openings or holes in an electrically conductive cylinder or surface shown in FIGS. 3 and 4, and in each opening said film may be in contact with one or more electrodes which are insulated from each other and which can be separately connected via coaxial or other cables to a suitable measuring instrument. Also, the electrically conductive layer 2 could be applied by painting, spraying or dipping. Further, the electrode may have any suitable shape, such as round, spherical, rectangular or combinations thereof. An example of this is shown in FIG. 5 where the piezoelectric film 1 has been applied around the edge of the electrically conductive sleeve 4 and over the circular electrode 5, the sensitivity area of the probe being 360° in a plane at right angles to the sleeve 4.

What I claim and desire to secure by letters patent is:

1. An ultrasonic detector device for converting ultrasonic signals into electrical signals, comprising
   an electrode,
   an electrically conductive casing enclosing the electrode so as to form a shield therefor,
   an opening in the casing around a distal end of the electrode,
   a piezoelectric film applied on and extending beyond the entire end surface of the distal end of the electrode,
   a thin, electrically conductive layer exclusively on the side of the film opposite to the electrode, and
   connection means electrically connecting the shield and the electrically conductive layer.

2. An ultrasonic detector device as claimed in claim 1, comprising an insulating body which fixes the distal end of the electrode in the casing and bridges the gap in said opening between the distal end of the electrode and the shield.

3. An ultrasonic detector device as claimed in claim 1, wherein the electrically conductive layer extends over the entire opening into electrical contact with the shield, thus also forming said connection means.

4. An ultrasonic detector device as claimed in claim 3, wherein the electrically conductive layer is applied by painting, spraying or dipping.

5. An ultrasonic detector device as claimed in claim 1, wherein the electrode is in the form of a rod.

6. An ultrasonic detector device as claimed in claim 1, wherein the electrode consists of an acoustically absorbing material of essentially higher acoustic impedance than that of the piezoelectric film.

7. An ultrasonic detector device as claimed in claim 1, wherein the piezoelectric film is glued to the electrode.

8. An ultrasonic detector device as claimed in claim 1, wherein the casing has several openings with a separate electrode disposed in each opening.

9. An ultrasonic detector device as claimed in claim 1, wherein the shield, the thin electrically conductive layer and the connection means entirely surround the electrode except at the proximal end thereof.

10. An ultrasonic detector device as claimed in claim 1, wherein the end surface of the distal end of the electrode, the surface of the insulating body bridging the gap, and the surface of the casing round the opening essentially lie on a level with each other.

* * * * *